United States Patent
Yuasa et al.

(10) Patent No.: US 8,298,387 B2
(45) Date of Patent: Oct. 30, 2012

(54) REACTIVE OXYGEN SPECIES MEASURING DEVICE

(76) Inventors: Makoto Yuasa, Soka (JP); Fumio Mizoguchi, Tokyo (JP); Hitoshi Takebayashi, Tsukuba (JP); Masahiko Abe, Noda (JP); Masumi Koishi, Sagamihara (JP); Shigeru Kido, Ishikawa-gun (JP); Masamitsu Nagahama, Kitakatsushika-gun (JP); Masayuki Kawasaki, Soka (JP); Masahiko Yokosuka, Mito (JP); Takashi Ishihara, Saitama (JP); Rizwangul Ibrahim, Abiko (JP)

( * ) Notice: Subject to any disclaimer, the term of this patent is extended or adjusted under 35 U.S.C. 154(b) by 989 days.

(21) Appl. No.: 10/547,142

(22) PCT Filed: Feb. 24, 2004

(86) PCT No.: PCT/JP2004/002112
§ 371 (c)(1),
(2), (4) Date: Oct. 25, 2005

(87) PCT Pub. No.: WO2004/074828
PCT Pub. Date: Sep. 2, 2004

(65) Prior Publication Data
US 2006/0289313 A1  Dec. 28, 2006

(30) Foreign Application Priority Data
Feb. 24, 2003  (JP) .................................. 2003-046392

(51) Int. Cl.
*C12Q 1/32* (2006.01)
(52) U.S. Cl. ......... 204/403.01; 204/403.02; 204/403.11; 205/777.5; 205/782

(58) Field of Classification Search .......... 204/403.01–403.15; 205/777.5–778, 205/782; 600/318–347, 365
See application file for complete search history.

(56) References Cited

U.S. PATENT DOCUMENTS
4,957,615 A * 9/1990 Ushizawa et al. ............. 204/415
(Continued)

FOREIGN PATENT DOCUMENTS
JP   62-180263   8/1987
(Continued)

OTHER PUBLICATIONS

Scheller, W, Jin, W, Ehrentreich-Forster, E, Ge, B, Lisdat, F, Buttemeier, R., Wollenberger, U., Scheller, F. W., Cytochrome C Based Superoxide Sensor for In Vivo Application, 1999, Electroanalysis, 11, 703-706.*

(Continued)

*Primary Examiner* — Keith Hendricks
*Assistant Examiner* — Bach Dinh
(74) *Attorney, Agent, or Firm* — DLA Piper LLP (US)

(57) ABSTRACT

A reactive oxygen species measuring device according to the present invention comprises a reactive oxygen species sensor provided with an electrode assembly capable of detecting the presence of reactive oxygen species or the like in terms of an electric current, a power source means for applying a measuring voltage to the reactive oxygen species sensor, and a reactive oxygen species concentration measuring means for measuring a concentration of the reactive oxygen species or the like from the current detected by the reactive oxygen species sensor. According to the present invention, a concentration of reactive oxygen species or the like such as in vivo or in vitro superoxide anion radical ($O_2^-$.) can be measured reliably, and the entire device can be formed in a smaller size and always mounted to a living body.

10 Claims, 5 Drawing Sheets

U.S. PATENT DOCUMENTS

| | | | |
|---|---|---|---|
| 5,186,808 A * | 2/1993 | Yamaguchi et al. | 204/403.1 |
| 6,565,509 B1 * | 5/2003 | Say et al. | 600/365 |
| 7,025,734 B1 * | 4/2006 | Ellis et al. | 600/585 |
| 2002/0045808 A1 * | 4/2002 | Ford et al. | 600/347 |
| 2005/0077192 A1 * | 4/2005 | Yuasa et al. | 205/775 |

FOREIGN PATENT DOCUMENTS

| | | | |
|---|---|---|---|
| JP | 2-1537 | | 1/1990 |
| JP | 2000-60807 | | 2/2000 |
| JP | 2002-245177 | | 8/2002 |
| JP | 2003-24285 | | 1/2003 |
| JP | 2001-387899 | * | 2/2003 |

OTHER PUBLICATIONS

Bhyrappa P., Bhavana P., Meso-tetrathienylporphyrins: Electrochemical and Axial Ligation Properties, 2001, Chemical Physics Letters, 349, pp. 399-404.*

Medford et al. NMR Studies of Nonplanar Porphyrins, Part 1. Axial Ligand Orientation in Highly Nonplanar Porphyrins, 1997, J.Chem. Soc., Perkin Trans., 2, pp. 833-837.*

Asako Shiozawa, O Sensor to shiteno kobunshika . . . , Superoxide Sensor Based on Electrode . . . , Sep. 18, 2002, p. 3717, vol. 51, No. 14, The society of Polymer Science, Japan.

Makoto Yuasa et al., Cobalt oyobi tetsu porphyrin . . . , Electrocatalytic Abilities of Reduction of . . . , Aug. 25, 2000, pp. 242-245, The Material Technology Association, Japan.

Juan Chen et al., Superoxide sensor based on hemin modified electrode, Sensors and Actuators, 2000, pp. 115-120, Elsevier Science B.V.

A. Brunet, et al. and Analusis (European Journal of Analytical Chemistry), Advantages and limits of the electro chemical method using Nafion and . . . , 2000, pp. 469-474.

Tomohisa Kasanuki et al., Hydrogen Peroxide Sensor Based on Carbon Paste Electrode Containing a metal porphyrin complex, Dec. 4, 2001, pp. 427-429, Chemical Sensors, Japan.

Barry W. Allen et al., Electrode Materials for nitric oxide detection, 2000, pp. 75-84, Nitric Oxide (Academic Press).

C.J. McNeil et al., Application of the Electrochemistry of Cytochrome . . . , 1989, pp. 89-96, Harwood Academic Publishers GmbH, England.

Michael J. Tarlov, Electron-Transfer Reaction of Cytochrome . . . , 1991, pp. 1847-1849, American Chemical Society, U.S.

Jonathan M. Cooper, Direct electron transfer reactions between immobilized cytochrome . . . , 1993, pp. 267-275, J. Electroanal Chem. (Elsevier Sequoia S.A.).

* cited by examiner

REACTIVE OXYGEN SPECIES MEASURING DEVICE

TECHNICAL FIELD

The present invention relates to a reactive oxygen species measuring device for measuring reactive oxygen species such as an in vivo or in vitro superoxide anion radical ($O_2^-$.), hydrogen peroxide, .OH, NO, $ONOO^-$.

BACKGROUND ART

In general, a superoxide anion radical ($O_2^-$.) which is a reactive oxygen species is produced in vivo by the oxidation of xanthine as well as hypoxanthine to uric acid by xanthine/xanthine oxidase (XOD) and the reduction of the enzyme by hemoglobin, and the like, and has an important role in association with the in vivo synthesis of a physiologically active substance, a sterilizing effect, an aging phenomenon and the like. On the other hand, it is alleged that various reactive oxygen species derived from the superoxide anion radical cause various diseases such as a cancer. Therefore, the measurement of a concentration of reactive oxygen species including an in vivo superoxide anion radical is considered to be important to specify the various diseases.

The superoxide anion radical, if no substrate exists, is converted into hydrogen peroxide and oxygen molecule ($O_2$) by a disproportionating reaction, as indicated in an equation (1). The disproportionating reaction comprises the production of $HO_2$. by the addition of proton to the superoxide anion radical, the production of hydrogen peroxide and oxygen molecule by the reaction of $HO_2$. and oxygen molecule, and the production of hydrogen peroxide and oxygen molecule by the collision of $HO_2$. and $HO_2$. (equations (1) to (4)).

$$2H^+ + 2O_2^-. \rightarrow H_2O_2 + O_2 \tag{1}$$

$$H^+ + O_2^-. \rightarrow HO_2. \tag{2}$$

$$HO_2. + O_2^-. + H^+ \rightarrow H_2O_2 + O_2 \tag{3}$$

$$HO_2. + HO_2^-. \rightarrow H_2O_2 + O_2 \tag{4}$$

In this reaction system, the superoxide anion radical acts as an electron acceptor (an oxidizing agent), an electron donor (a reducing agent) and a hydrogen ion acceptor (a base), and an attempt has been made to measure a concentration of a superoxide anion radical, utilizing the natures of first two of the donor and the acceptor. For example, an attempt has been made to measure a concentration of a superoxide anion radical, utilizing the reaction of conversion from ferri-cytochrome c (trivalent) to ferro-cytochrome c (divalent), the reaction of production of formazane blue from nitro-tretrazolium blue (NBT) and the reducing reaction of tetranitromethane (TNM). All of these measurements have been made by an in vitro measuring process.

On the other hand, reviews have been made for a process for quantitatively detecting a concentration of an in vivo superoxide anion radical. For example, McNeil et al, Tatiov et al and Cooper et al have reported that a concentration of a superoxide anion radical can be electrochemically detected by an enzyme electrode (cytochrome c-fixed electrode) fabricated by decorating a surface of an electrode of gold or platinum with N-acetyl cysteine, and S—Au bonding and fixing, to the resulting surface, a protein such as cytochrome c which is a metal protein based on an iron complex called heme for oxidation-reduction (see the following Documents 1 to 3).

Document 1
C. J. McNeil et al. Free Radical Res. Commun., 7, 89 (1989)
Document 2
M. J. Tariov et al. J. Am. Chem. Soc. 113, 1847 (1991)
Document 3
J. M. Cooper, K. R. Greenough and C. J. McNeil, J. Electroan al. Chem., 347, 267 (1993)

The measuring principle of this detecting method is as follows: Cytochrome c (trivalent) (cyt.c ($Fe^{3+}$)) is reduced into cytochrome c (divalent) (cyt.c ($Fe^{2+}$)) by reacting with a superoxide anion radical, as shown in an equation (5). Then, the cytochrome c (divalent) resulting from the reduction is re-oxidized electrochemically by $O_2^-$., as shown in an equation (6), and an oxidizing current at that time is measured, thereby quantitatively detecting a concentration of the superoxide anion radical indirectly.

$$\text{cyt.c}(Fe^{3+}) + O_2^-. \rightarrow \text{cyt.c}(Fe^{2+}) + O_2 \tag{5}$$

$$\text{cyt.c}(Fe^{2+}) \rightarrow \text{cyt.c}(Fe^{3+}) + e^- \tag{6}$$

However, the cytochrome c is an electron-transferring protein existing on a film of mitochondria within bio-cells and hence, to fabricate an electrode having the cytochrome c fixed thereon in an amount enough for the measurement, a large number of cells on the order of $10^5$-$10^6$ are required, and there is a problem that the enzyme used is deactivated within several days. Therefore, it has been desired to develop an electrode which is capable of detecting active oxygen species such as a superoxide anion radical without need for a large amount of an enzyme and without the problem of the deactivation of the enzyme.

Therefore, the present applicant has proposed, in Japanese Patent Application No. 2000-387899, an reactive oxygen species electrode comprising a polymerized film of a metalloporphyrin complex formed on a surface of a conductive member, an active oxygen species concentration measuring sensor including such an active oxygen species electrode, a counter electrode and a reference electrode, and a process for detecting reactive oxygen species in a sample by measuring an electric current produced between a metal in the polymerized film of the metalloporphyrin and reactive oxygen species by the sensor.

This is based on that the electrode assembly comprising the polymerized film of the metalloporphyrin complex having a metal ion introduced into the center of a porphyrin compound, which film has been formed on the surface of the conductive member, is capable of detecting the presence and concentration of the reactive oxygen species without need for a large amount of an enzyme and without the deactivation problem.

DISCLOSURE OF THE INVENTION

It is an object of the present invention to provide an reactive oxygen species measuring device with the present applicant's proposal further developed, which is capable of reliably measuring a concentration of a reactive oxygen species such as an in-vivo or in-vitro superoxide anion radical ($O_2^-$.), which can be small-sized in its entirety and can be always mounted to a living body, so that measured data can be transmitted to a remote location, and the health condition or the like of the living body provided in the remote location can be returned to a reactive oxygen species measuring location for information, thus monitoring the health condition and the like of the living body by measuring and monitoring the reactive oxygen species.

To achieve the above object, according to a first aspect and feature of the present invention, there is provided a reactive oxygen species measuring device comprising a reactive oxygen species sensor provided with an electrode assembly capable of detecting the presence of reactive oxygen species in terms of an electric current, a power source means for applying a measuring voltage to the reactive oxygen species sensor, and a reactive oxygen species concentration measuring means for measuring a concentration of the reactive oxygen species from the current detected by the reactive oxygen species sensor. The arrangement of the reactive oxygen species measuring device as described above ensures that when an appropriate measuring voltage from the power source means is applied to the reactive oxygen species sensor, the electrode of the reactive oxygen species sensor can detect the presence of the reactive oxygen species or the like in terms of the electric current, and the concentration of the reactive oxygen species or the like can be determined from the electric current detected by the reactive oxygen species concentration measuring means.

The reactive oxygen species concentration measuring means includes an external output means for delivering the measured concentration of the reactive oxygen species or the like to the outside, and may be arranged in association with a remotely monitoring means adapted to monitor the concentration of the reactive oxygen species or the like under the reception of the output from the external output means. Thus, the health condition of the living body can be monitored in a remote place, using the remotely monitoring means.

The remotely monitoring means includes a communication means for transmitting and receiving data to or from the reactive oxygen species measuring device, an arithmetic means adapted to perform a data processing for the concentration of the reactive oxygen species or the like received from the external output means, and a display means for displaying the concentration of the reactive oxygen species or the like and the result of the data processing obtained by the arithmetic means. In the reactive oxygen species measuring device, the external output means is comprised of a communication means for transmitting and receiving the data to and from the remotely monitoring means, and a display means for displaying the concentration of the reactive oxygen species or the like and the data received from the remotely monitoring means. With such arrangement, in the remotely monitoring means, the data processing for the concentration of the reactive oxygen species can be conducted by the arithmetic means to determine the health condition of a living body such as human being as a subject of measurement and an in vitro environmental condition, and the health condition of the living body and the in vitro environmental condition can be monitored by displaying them and the concentration of the reactive oxygen species of the like by the display means. Further, the health condition and of the living body and the like determined in the remote place can be returned to the active oxygen species measuring device through the communication means in both the remotely monitoring means and the active oxygen species measuring device, and displayed by the display means and thereby informed to a person. In addition, by using the remotely monitoring means as a base station, it is possible to make a simultaneous access to a plurality of reactive oxygen species measuring devices, to provide a centralized management of various data, and to carry out the data processing arithmetically inoperable in the reactive oxygen species measuring device to transmit necessary obtained data to the reactive oxygen species measuring device.

The present invention has a feature that the delivery and reception of the data between the active oxygen species measuring device and the remotely monitoring means are carried out through a radio or wire propagation system. With such arrangement, when the radio propagation system is used, the monitoring of the concentration of the reactive oxygen species or the like can be controlled remotely regardless of the magnitude of the distance between the remotely monitoring means and the reactive oxygen species measuring device, and particularly, even when the reactive oxygen species measuring device is moved, the operation always normal can be continued. For the radio propagation system, a known method employing an electric wave, infrared rays, ultraviolet rays or an ultrasonic wave, or any of various communication technologies such as an internet, a satellite communication and the like can be utilized. On the other hand, when the wire propagation system is used, the reliable transmission and reception of data are possible, and further, an electric wave interference cannot be exerted to other electronic equipments, and the wire propagation system can be used, for example, in a hospital or the like.

Another feature of the present invention is that the communication means and the display means in the reactive oxygen species measuring device are formed in a mobile phone to deliver and receive the data to and from the remotely monitoring means through an internet. Thus, the measurement of reactive oxygen species or the like can be achieved using the mobile phone excellent in portability or mobility and further by conducting the interchange of data through an internet, leading to a facilitated measuring operation. In addition, the measurement is possible at any time in any area if there is a telephone service in this area, and the reactive oxygen species can be measured in reliable correspondence to an emergency, whereby the monitoring of the health of a living body can be achieved.

It is preferable that the electrode of the active oxygen species sensor is formed into a shape capable of detecting the presence of an in-vivo active oxygen species or the like in terms of an electric current. Thus, by attaching the electrode to a human body or an animal, an in vivo reactive oxygen species or the like can be measured, and further can be continued to be measured constantly.

The power source means may be formed so that the measuring voltage to be applied to the reactive oxygen species sensor can be controlled variably. Thus, an appropriate measuring voltage corresponding to a reactive oxygen species or the like to be measured can be applied to the reactive oxygen species sensor to measure a reactive oxygen species or the like as a subject of measurement with a good accuracy.

The reactive oxygen species concentration measuring means may include at least one of a display means for displaying a concentration of reactive oxygen species or the like determined based on an electric current detected by said reactive oxygen species sensor, and an external output means for delivering data to the outside. Thus, the measured concentration of the reactive oxygen species or the like can be clearly displayed by the display means, and the concentration of the reactive oxygen species or the like can be transmitted to a remote place or location by the external output means and monitored remotely.

More specifically, the electrode assembly of the reactive oxygen species sensor may be formed to have, on its surface, an element capable of detecting the presence of reactive oxygen species or the like in terms of an electric current. Thus, by placing the element on the surface of the electrode assembly in a region where an in vivo or in vitro reactive oxygen species or the like exists, a concentration of the in vivo or in vitro a reactive oxygen species or the like can be measured reliably.

The element capable of detecting the presence of reactive oxygen species or the like in terms of an electric current may be formed by at least one of a polymerized film of a metalloporphyrin complex, a redox polymer or its derivative, a metal composite and a complex-based compound. The element formed as described above ensures that a concentration of active oxygen species or the like can be measured with a good accuracy and reliably.

The metalloporphyrin complex is represented by the following formula (I) or (II):

(I)

wherein M indicates a metal ion selected from the group consisting of iron, manganese, cobalt, chromium and iridium; at least one of four Rs is any one of thiofuryl, pyrrolyl, furyl, mercaptophenyl, aminophenyl and hydroxyphenyl groups; and each of other Rs indicates any of the above-described groups, or alkyl group, aryl group or hydrogen;

(II)

wherein each of M and R has the above-described meaning, and at least one of two Ls is an nitrogen-based axial ligand such as imidazole and its derivative, pyridine and its derivative, aniline and its derivative, histidine and its derivative, and trimethylamine and its derivative, a sulfur-based axial ligand such as thiophenol and its derivative, cysteine and its derivative, and methionine and its derivative, or an oxygen-based axial ligand such as benzoic acid and its derivative, acetic acid and its derivative, phenol and its derivative, an aliphatic alcohol and its derivative or water; and the other L indicates any of the above-described axial ligands or no ligand.

Thus, the metalloporphyrin complex can be formed reliably on the surface of the electrode assembly, thereby providing an electrode assembly excellent in sensitivity.

The porphyrin compound forming the metalloporphyrin complex is one selected from the group consisting of 5,10, 15,20-tetrakis(2-thienyl)porphyrin, 5,10,15,20-tetrakis(3-thienyl)porphyrin, 5,10,15,20-tetrakis(2-pyrrolyl)porphyrin, 5,10,15,20-tetrakis(3-pyrrolyl)porphyrin, 5,10,15,20-tetrakis(2-furyl)porphyrin, 5,10,15,20-tetrakis(3-furyl)porphyrin, 5,10,15,20-tetrakis(2-mercaptophenyl)porphyrin, 5,10,15,20-tetrakis(3-mercaptophenyl)porphyrin, 5,10,15,20-tetrakis(4-mercaptophenyl)porphyrin, 5,10,15,20-tetrakis(2-aminophenyl)porphyrin, 5,10,15,20-tetrakis(3-aminophenyl)porphyrin, 5,10,15,20-tetrakis(4-aminophenyl)porphyrin, 5,10,15,20-tetrakis(2-hydroxyphenyl)porphyrin, 5,10,15,20-tetrakis(3-hydroxyphenyl)porphyrin, 5,10,15,20-tetrakis(4-hydroxyphenyl)porphyrin, [5,10,15-tris(2-thienyl)-20-mono(phenyl)]porphyrin, [5,10,15-tris(3-thienyl)-20-mono(phenyl)]porphyrin, [5,10-bis(2-thienyl)-15,20-di(phenyl)]porphyrin, [5,10-bis(3-thienyl)-15,20-di(phenyl)]porphyrin, [5,10-bis(2-thienyl)-10,20-di(phenyl)]porphyrin, [5,10-bis(3-thienyl)-10,20-di(phenyl)]porphyrin, [5-mono(2-thienyl)-10,15,20-tri(phenyl)]porphyrin, [5-mono(3-thienyl)-10,15,20-tri(phenyl)]porphyrin. Thus, the metalloporphyrin complex can be formed reliably on the surface of the electrode assembly, thereby providing an electrode assembly excellent in sensitivity.

The reactive oxygen species measuring device according to the present invention is constructed and operated as described above and hence, the following excellent effects can be exhibited: A concentration of reactive oxygen species or the like such as in vivo or in vitro superoxide anion radical ($O_2^-$.) can be measured reliably, and the entire device can be formed in a smaller size and always mounted to a living body. In addition, the measured data can be transmitted to a remote place or location, and further, the health condition of a living body or the like determined in the remote place can be returned to a measuring place and informed, and thus, the health condition of the living body can be monitored by measuring and monitoring reactive oxygen species.

BRIEF DESCRIPTION OF THE DRAWINGS

FIG. 6(a) is a plan view showing a yet further embodiment of a reactive oxygen species sensor used in the reactive oxygen species measuring device according to the present invention with a cover removed, FIG. 6(b) is a vertical sectional view of the embodiment in FIG. 6(a), and a FIG. 6(c) is an exploded perspective view with a cover removed.

BEST MODE FOR CARRYING OUT THE INVENTION

An embodiment of the present invention will now be described with reference to FIGS. 1 to 7.

Figure 1:
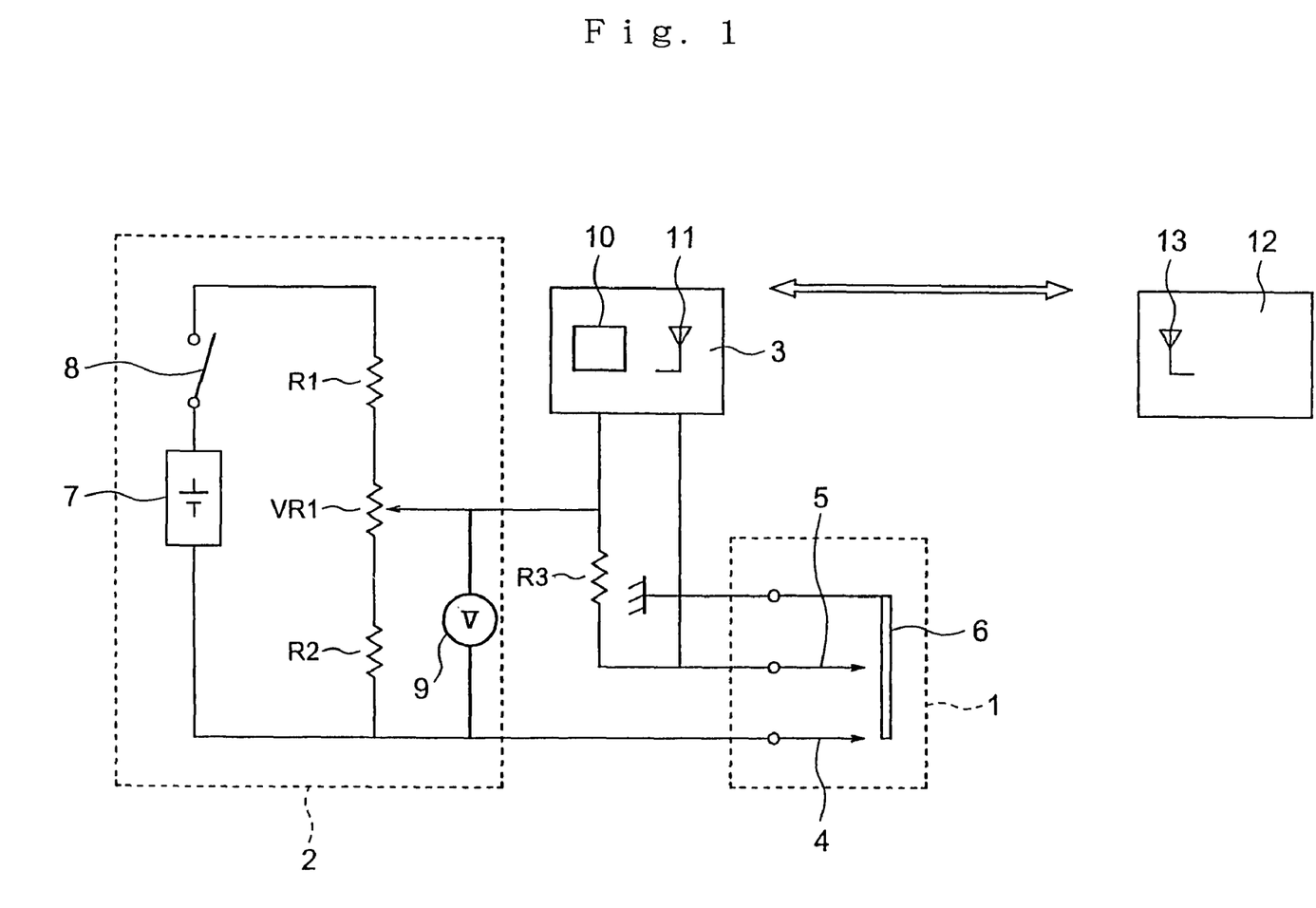
FIG. 1 is a circuit diagram showing one embodiment of an reactive oxygen species measuring device according to the present invention.

FIG. 1 shows one embodiment of a reactive oxygen species measuring device according to the present invention.

The reactive oxygen species measuring device of the present embodiment includes a reactive oxygen species sensor 1 provided with an electrode assembly capable of detecting the presence of reactive oxygen species in terms of an electric current, a power source means 2 for applying a measuring voltage to the active oxygen species sensor 1, and an active oxygen species concentration measuring means for measuring a concentration of active oxygen species from the electric current detected by the reactive oxygen species sensor 1.

The reactive oxygen species sensor 1 in the present embodiment is formed in a two-electrode type and constructed by a working electrode 4, a counter electrode 5 and a shield. It should be noted that the reactive oxygen species sensor 1 may be formed in a three-electrode type including a reference electrode which is not shown.

The power source means 2 is constructed with a switch 8, a potential divider resistor R1, a variable resistor VR1, a potential divider resistor R2 connected in series to a DC power source 7 such a button battery and a potentiostat, so that a measuring voltage can be delivered in a variable manner from ends of the variable resistor VR1 and a potential divider resistor R2. The measuring voltage is intended to be measured by a voltmeter 9. The measuring voltage to be applied to the reactive oxygen species sensor 1 by the power source means 2 is controlled variably in accordance with reactive oxygen species to be measured by changing the resistance value of the variable resistor VR1. For example, the measuring voltage may be 0.5 V for a superoxide anion radical, −0.8 V for oxygen molecule ($O_2$), −1.0 V for hydrogen peroxide ($H_2O_2$), and 0.6 V for nitrogen monoxide.

The measuring voltage from the power source means 2 is applied through a device resistor 3 to the counter electrode 5 and the working electrode of the reactive oxygen species sensor 1.

Further, a reactive oxygen species concentration measuring means 3 is connected to the reactive oxygen species sensor 1 for measuring the concentration of the reactive oxygen species through the amplification of a very weak current flowing between the counter electrode 5 and the working electrode 4 of the reactive oxygen species sensor 1 and corresponding to the concentration of the reactive oxygen species. The reactive oxygen species concentration measuring means 3 includes a display means 10 for displaying the concentration of the reactive oxygen species determined based on the electric current detected by the reactive oxygen species sensor 1, and an external output means 11 for delivering the measured concentration to the outside by transmission or the like. At least one of the display means 10 and the external output means 11 may be provided. When the external output means 11 is provided, a remotely monitoring means 12 including a receiving means 13 may be mounted to remotely monitor the concentration of the reactive oxygen species under the reception of the result of the detection of the concentration fed from the reactive oxygen species concentration measuring means 3. More specifically, the a remotely monitoring means 12 includes the receiving means 13, and may be formed to remotely monitor the concentration of the active oxygen species or the like by receiving the result of the detection of the concentration fed from the external output means 11 of the active oxygen species concentration measuring means to determine the health condition of a living body as a subject of measurement and the in vitro environmental condition by the arithmetic operation conducted based on the concentration of the reactive oxygen species by an arithmetic means (not shown), and displaying the concentration of the reactive oxygen species as well as the health condition of the living body as the subject of measurement and the in vitro environmental condition by a display means (likewise not shown).

The working electrode 4 as an electrode of the reactive oxygen species sensor 1 will be further described below.

The working electrode 4 may be formed into a shape enabling the detection of the presence of an in-vivo active oxygen species in terms of an electric current, e.g., a fine needle-shape capable of being inset into the living body from the outside, a very small catheter-shape capable of being inserted into a blood vessel, or a shape capable of being bonded to a surface of a skin, e.g., a shaft portion of a pierce. Thus, the working electrode 4 can be mounted to a human body to measure reactive oxygen species or the like in the human body or to measure an in vivo reactive oxygen species or the like at all times. The specific construction of each of the working electrode 4 and the counter electrode 5 will be described below.

The working electrode 4 may be formed to be provided, on its surface, with an element capable of detecting the presence of reactive oxygen species or the like in terms of an electric current. Thus, it is possible to reliably measure a concentration of in vivo reactive oxygen species or the like by placing the element in an area of a living body where reactive oxygen species or the like exists.

The element of the working electrode 4 capable of detecting the presence of the reactive oxygen species or the like in terms of the electric current may be formed of at least one of a polymerized film of a metalloporphyrin complex, a redox polymer or its derivative, a metal composite and a complex-based compound. By using the element formed as described above, the concentration of active oxygen species or the like can be measured with a good accuracy and reliably.

The formation of the polymerized film of a metalloporphyrin suitable as a material for the working electrode 4 itself and a material for the surface film will be described below.

A conductive member constituting the working electrode 4 is particularly not limited, and any member can be used if it is a member commonly used for an electrode, and for example, the member which can be used includes carbons such as glassy carbon (GC), graphite, pyrolytic graphite (PG), highly oriented pyrolytic graphite (HOPG) and activated carbon; a rare metal such as platinum, gold and silver; or $In_2O_3/SnO_2$ (ITO) or the like. Among them, particularly, it is preferable to use grassy carbon, taking an economy, a workability and a lightness into consideration. The shape of the conductive member is particularly not limited, and may be any shape if it can be used for the electrode. The conductive member can be any of various shapes such as a columnar shape, a prismatic shape, a needle-shape and a fiber-shape. For example, in order to measure a concentration of reactive oxygen species in a living body, it is preferable that the material is of a needle-shape, a catheter-shape or a pierce shaft-shape, as described above.

Examples of a metal porphyrin complex used for the formation of the metalloporphyrin complex polymerized film formed on the surface of the conductive member of the working electrode 4 include those represented by a formula (I) or (II):

(I)

wherein M indicates a metal ion selected from the group consisting of iron, manganese, cobalt, chromium and iridium; at least one of four Rs is any one of thiofuryl, pyrrolyl, furyl, mercaptophenyl, aminophenyl and hydroxyphenyl groups; and each of other Rs indicates any of the above-described groups, or alkyl group, aryl group or hydrogen; and (II)

wherein each of M and R has the above-described meaning, and at least one of two Ls is an nitrogen-based axial ligand such as imidazole and its derivative, pyridine and its derivative, aniline and its derivative, histidine and its derivative, and trimethylarnine and its derivative, a sulfur-based axial ligand such as thiophenol and its derivative, cysteine and its derivative, and methionine and its derivative, or an oxygen-based axial ligand such as benzoic acid and its derivative, acetic acid and its derivative, phenol and its derivative, an aliphatic alcohol and its derivative or water; and the other L indicates any of the above-described axial ligands or no ligand.

The metalloporphyrin complex represented by the above formula (I) or (II) is a complex compound having a metal ion coordinated in a porphyrin compound. The porphyrin compound is a cyclic compound having four pyrrole rings alternately bonded to four methyl groups at α sites and four nitrogen atoms located to face to the center. The complex compound (metal porphyrin complex) can be formed by incorporating a metal atom at the center site. To form such complex compound, a metal atom may be introduced into the center of porphyrin using a metal complex forming method usually used, e.g., a method of metalation or the like. In the present invention, the metal ion which can be introduced into the center of the porphyrin compound includes various metal ions such as iron, manganese, cobalt, chromium and iridium.

Depending on the type of reactive oxygen species to be measured, suitable one of such metal ions may be used. Preferable examples are as follows: For example, if a superoxide anion radical is to be measured, iron, manganese or cobalt may be used. If oxygen in the state of a molecule is to be measured, iron, cobalt, manganese chromium or iridium may be used. If hydrogen peroxide is to be measured, iron or manganese may be used. Further, if OH, NO, ONOO⁻ or the like is to be measured, iron or manganese may be used.

Preferable examples of the porphyrin compound used in the present invention include those in which at least one of four sites of site numbers 5, 10, 15 and 20 according to the IUPAC nomenclature in non-substituted porphyrin is substituted by any of thiofuryl, pyrrolyl, furyl, mercaptophenyl, aminophenyl and hydroxyphenyl groups, and each of other sites is any of the above-described substituting groups, or alkyl group, aryl group or hydrogen. Illustrative of particular examples are 5,10,15,20-tetrakis(2-thienyl)porphyrin, 5,10,15,20-tetrakis(3-thienyl)porphyrin, 5,10,15,20-tetrakis(2-pyrrolyl)porphyrin, 5,10,15,20-tetrakis(3-pyrrolyl)porphyrin, 5,10,15,20-tetrakis(2-furyl)porphyrin, 5,10,15,20-tetrakis(3-furyl)porphyrin, 5,10,15,20-tetrakis(2-mercaptophenyl)porphyrin, 5,10,15,20-tetrakis(3-mercaptophenyl)porphyrin, 5,10,15,20-tetrakis(4-mercaptophenyl)porphyrin, 5,10,15,20-tetrakis(2-aminophenyl)porphyrin, 5,10,15,20-tetrakis(3-aminophenyl)porphyrin, 5,10,15,20-tetrakis(4-aminophenyl) porphyrin, 5,10,15,20-tetrakis(2-hydroxyphenyl)porphyrin, 5,10,15,20-tetrakis(3-hydroxyphenyl)porphyrin, 5,10,15,20-tetrakis(4-hydroxyphenyl)porphyrin, [5,10,15-tris(2-thienyl)-20-mono(phenyl)]porphyrin, [5,10,15-tris(3-thienyl)-20-mono(phenyl)]porphyrin, [5,10-bis(2-thienyl)-15,20-di(phenyl)] porphyrin, [5,10-bis(3-thienyl)-15,20-di(phenyl)]porphyrin, [5,10-bis(2-thienyl)-10,20-di(phenyl)]porphyrin, [5,10-bis(3-thienyl)-10,20-di(phenyl)]porphyrin, [5-mono(2-thienyl)-10,15,20-tri(phenyl)]porphyrin, [5-mono(3-thienyl)-10,15,20-tri(phenyl)]porphyrin, and the like.

Among the ligands indicated by L in the compound represented by the formula (II), examples of imidazole derivatives are methylimidazole, ethylimidazole, propylimidazole, dimethylimidazole, benzoimidazole or the like. Examples of pyridine derivatives are methylpyridine, methylpyridylacetate, nicotinamide, pyridazine, pyrimidine, pyrazine, triazine or the like. Examples of aniline derivatives are aminophenol, diaminobenzene or the like. Examples of histidine derivatives are histidine methyl ester, histamine, hippuryl-histidyl-leucine and the like. Examples of trimetylamine derivatives are triethylamine, tripropylamine and the like. Examples of thiophenol derivatives are thiocresol, mercaptophenol, mercaptobenzoic acid, aminothiophenol, benzene dithiol, methylbenzene dithiol and the like. Examples of cysteine derivatives are cysteine methyl ester, cysteine ethyl ester and the like. Examples of methionine derivatives are methionine methyl ester, methionine ethyl ester and the like. Examples of benzoic acid derivatives are salicylic acid, phthalic acid, isophthalic acid, terephthalic acid and the like. Examples of acetic acid derivatives are trifluoroacetic acid, mercaptoacetic acid, propionic acid, butyric acid and the like. Examples of phenol derivatives are cresol, hydroxybenzene and the like. Examples of aliphatic alcohol derivatives are ethyl alcohol, propyl alcohol and the like.

In the present invention, to form the polymerized film of the metal porphyrin complex on the surface of the conductive member of the working electrode 4, various polymerizing processes may be used such as an electrolytic polymerizing process, a solution polymerizing process, a heterogeneous polymerizing process and the like. Among them, the use of the electrolytic polymerizing process is preferred for forming the polymerized film. More specifically, a polymerized film of a metalloporphyrin can be formed on a surface of a conductive member by adding a suitable supporting electrolyte such as tetrabutyl ammonium perchlorate (TBAP: $Bu_4NClO_4$), tetrapropyl ammonium perchlorate (TPAP: $Pr_4NClO_4$) and tetraethyl ammonium perchlorate (TPAP: $Et_4NClO_4$) into an organic solvent such as dichloromethane, chloroform and carbon tetrachloride, and subjecting the resulting mixture to a two-electrode (working electrode/counter electrode) electrolysis or a three-electrode (working electrode/counter electrode/reference electrode) constant-potential, constant-current, reversible potential sweep and pulse-type electrolysis using a conductive member as a working electrode, a rare metal electrode such as a platinum (Pt) electrode or an insoluble electrode such as a titanium electrode, a carbon electrode and a stainless steel electrode as a counter electrode and a saturated calomel electrode (SCE) or a silver-silver chloride electrode as a reference electrode, thereby polymerizing the mixture.

The particular arrangement of a reactive oxygen species sensor 1 including electrodes such as a working electrode 4 a counter electrode 5 and the like will be described below with reference to FIGS. 2 to 5.

Figure 2:
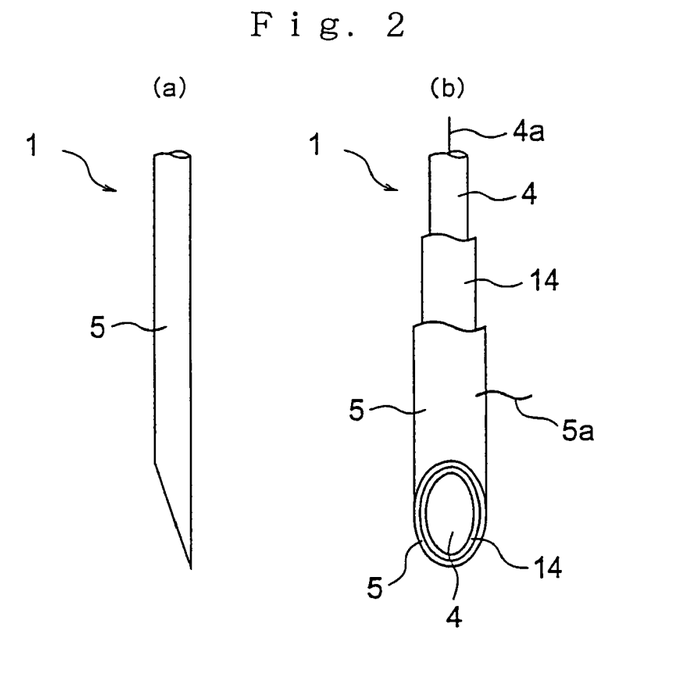
FIG. 2(a) is a side view showing one embodiment of a reactive oxygen species sensor used in the active oxygen species measuring device according to the present invention.
FIG. 2(b) is a left side view of the sensor shown in FIG. 2(a)

FIGS. 2(a) and (b) show a reactive oxygen species sensor 1 including a working electrode 4 and a counter electrode 5 formed integrally with each other to form a needle-shaped electrode assembly taking the in vivo measurement, the combined measurement and the clinical diagnosis/therapy into consideration. In the active oxygen species sensor 1 shown in FIG. 2, its outermost portion is formed as a counter electrode 5, and a conductive member forming the working electrode 4 is concentrically mounted within the counter electrode 5 with an electrically insulating material 14 interposed therebetween. Tip ends of the working electrode 4, the electrically insulating material 14 and the counter electrode 5 are cut obliquely to form a sharp needle point for finishing. A polymerized film of a metalloporphyrin as described above is formed on a portion of the working electrode 4 exposed to the outside from the tip end of the needle-shaped counter electrode 5. The working electrode 4 and the counter electrode 5 are formed so as to be electrically connected by lead wires 4a and 4a, respectively.

A material for forming the counter electrode 5 which can be used includes various materials, e.g., a rare metal such as platinum, gold and silver, titanium, a stainless steel, a corrosion-resistant alloy such as an iron-chromium alloy, carbons and the like, but because the counter electrode may be inserted into a living body in many cases, it is preferable to form the counter electrode using a high safety material (for example, a rare metal such as platinum, gold and silver, titanium, a stainless steel, carbons and the like). If the needle-shape active oxygen species sensor 1 is desired to be inserted into a living body, then it is preferable that the sensor 1 is formed so that the contour of the counter electrode 5 is as thin as possible, for example, on the order of 0.2 to 1.5 mm. If a reference electrode (not shown) is desired to be employed, then any of various reference electrodes may be usually employed such as a silver/silver chloride electrode and a mercury/mercuric chloride electrode, and a solid reference electrode can be employed.

The thickness of the polymerized film of the metalloporphyrin complex may be determined properly depending on the types of the electrodes and the metalloporphyrin complex and the type of reactive oxygen species to be measured, but it is preferable that the thickness is equal to or smaller than 1 µm from the viewpoints of the activity of the electrodes and the decoration stability.

FIGS. 3(a) and (b) show another reactive oxygen species sensor 1a formed into a needle-shape as in FIG. 2.

Figure 3:
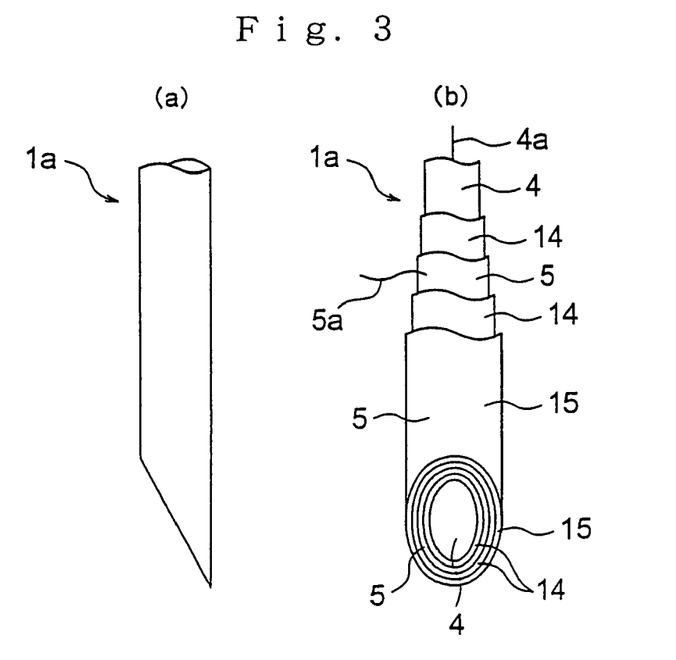
FIG. 3(a) is a side view showing another embodiment of a reactive oxygen species sensor used in the reactive oxygen species measuring device according to the present invention.
FIG. 3(b) is a left side view of the sensor shown in FIG. 2(a)

The reactive oxygen species sensor 1a of the embodiment shown in FIG. 3 is an improvement in the reactive oxygen species sensor 1 shown in FIG. 2 for the purpose of aiming to remove an unnecessary in vivo current, a current noise and the like and to enhance the sensitivity, the signal/noise ratio (S/N ratio) and the like. In an electrode assembly shown in FIG. 3, a working electrode 4 comprised of a conductive member is placed into an electrically insulating material 14 (a two-layer structure), and they are placed into a counter electrode 5 (a three-layer structure). Further, they are placed into an electrically insulating material 14 (a four-layer structure), and finally, an outer surface of the resulting thin tube is coated with a material such as a metal serving as an earth to form an earth portion 15. Tip ends of the working electrode 4, the electrically insulating material 14, the counter electrode 5, the electrically insulating material 14 and the earth portion 15 are cut obliquely to form a sharp needle point for finishing. A polymerized film of a metal porphyrin is formed on an end face of the conductive member of the working electrode 4.

The thickness of the polymerized film of the metalloporphyrin complex may be determined properly depending on the types of the electrodes and the metalloporphyrin complex and the type of reactive oxygen species to be measured, but it is preferable that the thickness is equal to or smaller than 1 µm from the viewpoints of the activity of the electrodes and the decoration stability.

The reactive oxygen species sensor 1a having the structure shown in FIG. 3 is also used for the combined measurement or the like and hence, a multi-layer structure having about ten several layers can be constructed. A material for forming the earth which can be used includes various materials, e.g., a rare metal such as platinum, gold and silver, titanium, a stainless steel, a corrosion-resistant alloy such as an iron-chromium alloy, carbons and the like, but because the earth may be inserted into a living body in many cases, it is preferable to form the earth using a high safety material (for example, a rare metal such as platinum, gold and silver, titanium, a stainless steel, carbons and the like).

Each of the reactive oxygen species sensors 1 and 1a shown in FIGS. 2 and 3 is capable of measuring reactive oxygen species by inserting the sharp tip end of the respective electrode section into a living body.

Figure 4:
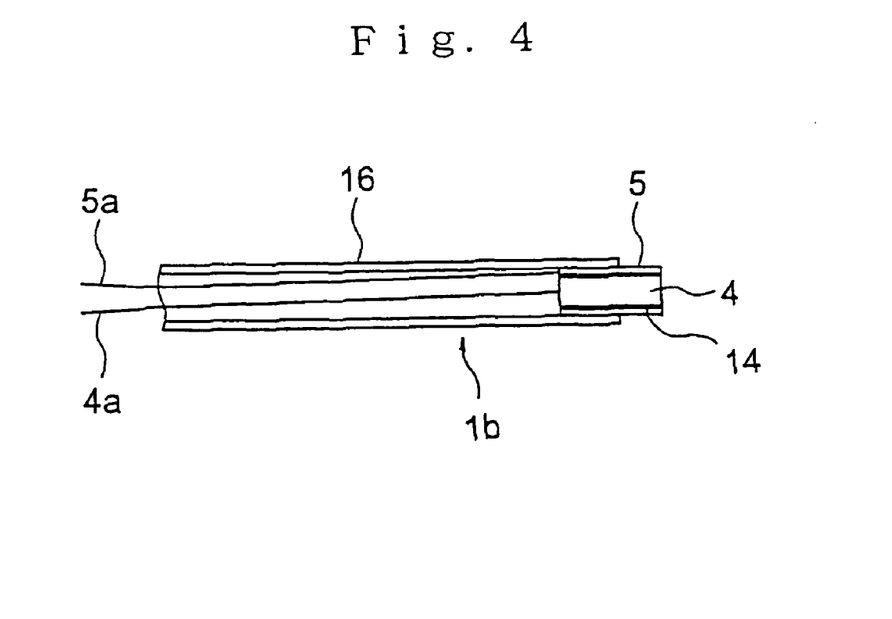
FIG. 4 is a side view showing a further embodiment of an active oxygen species sensor used in the active oxygen species measuring device according to the present invention.

FIG. 4 shows another reactive oxygen species sensor 1b formed into a catheter-shape.

The reactive oxygen species sensor 1b of the embodiment shown in FIG. 4 is constructed as follows: A thin electrode section comprising a working electrode 4, an electrically insulating material 14 and a counter electrode 5 as in FIG. 2 is formed in the sensor 1b, and a tip end of the electrode section is cut perpendicular to an axial direction for finishing. Further, the electrode section is secured to a tip end of a pipe 16 made of a resin and having a counter length on the order of 1 mm along with connected lead wires 4a and 5a of the working electrode 4 and the counter electrode 5. The resinous pipe 16 is formed of a material which is safe even if it is inserted into a living body.

The reactive oxygen species sensor 1b shown in FIG. 4 is capable of measuring reactive oxygen species or the like by inserting the thin electrode section into a living body, specifically, into a blood vessel, a lymphatic vessel, a digestive organ, any of internal organs and the like. A provision may be made for ensuring that the direction of advancement of the electrode section at the tip end can be freely changed by a remote manipulation. For example, the electrode section is mounted, slightly inclined with respect to an axial direction of the resinous pipe 16, so that the direction of advancement of the electrode section can be selected by rotating the resinous pipe 16 about an axis, or alternatively, a small-sized bimetal is mounted in the vicinity of the electrode section, so that the bimetal can be bent in any direction by controlling the supply of an electric current for the selection of the direction of advancement, or alternatively, a small-sized magnet is mounted on the electrode section, so that the direction of advancement of the small-sized magnet can be selected by applying a magnetic field from outside a living body.

Figure 5:
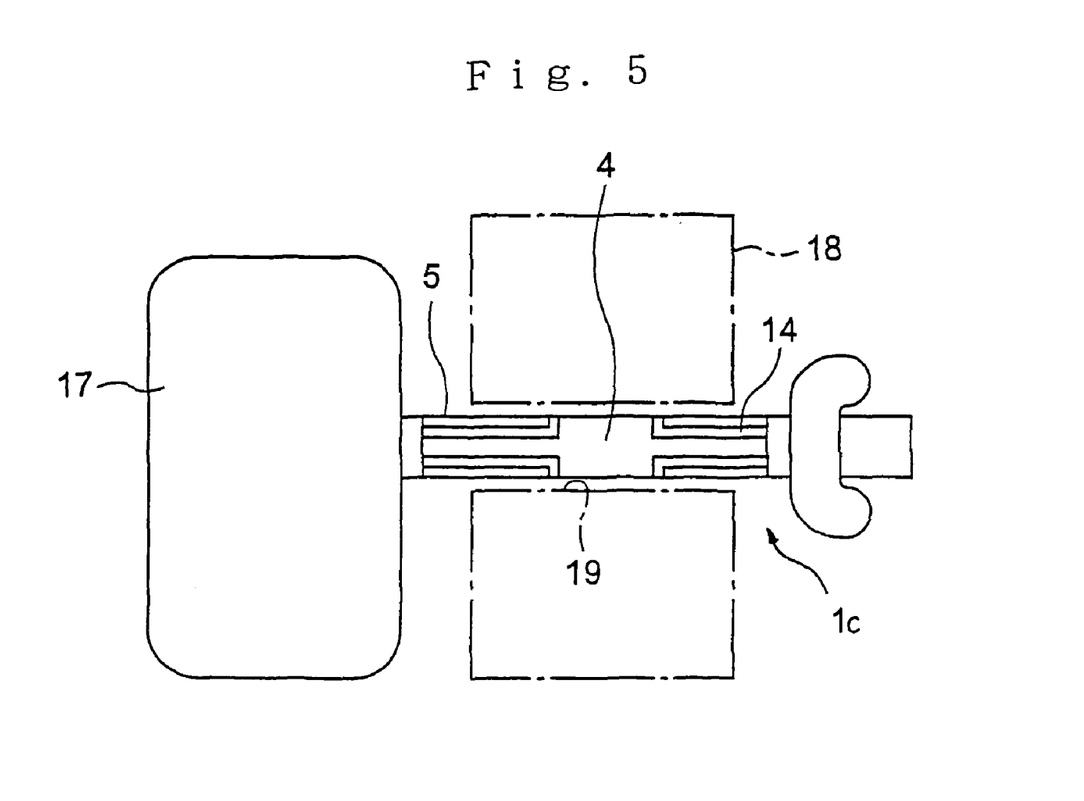
FIG. 5 is a side view showing a yet further embodiment of a reactive oxygen species sensor used in the reactive oxygen species measuring device according to the present invention.

FIG. 5 shows another reactive oxygen species sensor 1c formed into a pierce shaft-shape.

The reactive oxygen species sensor 1c shown in FIG. 5 is constructed as follows: A thin electrode section comprising a working electrode 4, an electrically insulating material 14 and a counter electrode as in FIG. 2 is formed in the sensor 1c, and the working electrode 4 inside the counter electrode 5 is exposed to an axially intermediate portion of the electrode section, while the electrically insulating material 14 is exposed to an outer peripheral surface of the electrode section. Further, the working electrode 4 and the counter electrode 5 are connected to a small-sized power source means 2 and an active oxygen species concentration measuring means 3 within a decorative portion 17 of a pierce.

The reactive oxygen species sensor 1c shown in FIG. 5 is capable of measuring reactive oxygen species or the like by inserting the thin electrode section through a pierce bore 19 in an ear 18.

Figure 6:
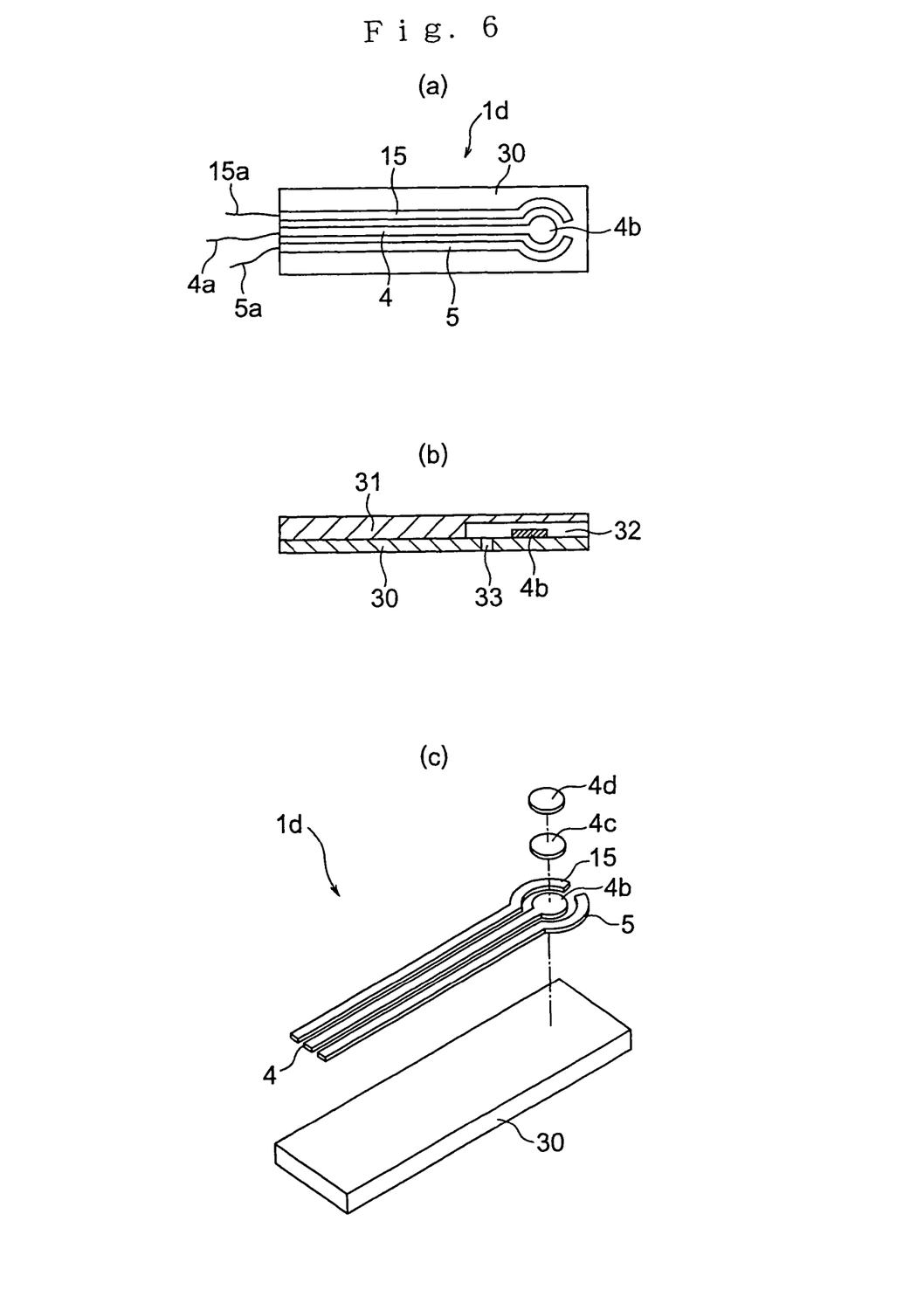

FIG. 6 shows a further reactive oxygen species sensor 1d formed into a chip-shape.

Although each of the embodiments 1, 1a, 1b and 1c is adapted to be pierced to inserted into a living body, or brought into contact with the living body, the reactive oxygen species sensor 1d of the embodiment shown in FIG. 6 is adapted to measure a concentration of reactive oxygen in a liquid to be measured such as a small amount of blood removed from a living body. FIG. 6 shows the reactive oxygen species sensor 1d in an exaggerated manner for convenience of the explanation, but the chip has a size of 5 mm×20 to 30 mm in a planar shape with a thickness of on the order of 0.5 to 1.0 nm. The active oxygen species sensor 1d includes a working electrode 4 centrally formed on an insulting substrate 30 of a glass a resin, a ceramic or the like, and a counter electrode 5 and an earth portion 15 formed on opposite sides of the working electrode 4. A material for forming each of the working electrode 4, the counter electrode 5 and the earth portion 15, which can be used, includes gold, platinum, nickel, nickel-phosphorus plating material, a stainless steel, carbon or another conductive metal and the like. When such a material is used to form a pattern on the insulating substrate 30, any of an electroless treatment as a wet surface treatment and a vacuum deposition an ion-plating, a coating/baking by an ink jet and the like as a dry surface treatment may be selected. Further, as in the previous embodiments, a carbon layer 4c is formed thinly on a surface of a circular measuring portion 4b at an end of the central working electrode 4, and a polymerized film 4d of a metalloporphyrin complex is formed on the carbon layer 4c. The carbon layer 4c may be provided, as required, from the relation to a material or the like for the measuring portion 4b when the polymerized film 4d of a metal porphyrin complex on the carbon layer 4c is provided, but the carbon layer 4c may be omitted. The carbon layer 4c may be formed by a process similar to that for each of the working electrode 4, the counter electrode 5 and the earth portion 15. The polymerized film 4d of a metal porphyrin complex can be formed using any of various polymerizing processes such as an electrolytic polymerizing process, a solution polymerizing process and a heterogeneous polymerizing process as in each of the previous embodiments. The working electrode 4, the counter electrode 4 and the earth portion 15 are formed so that they are electrically connected by respective lead wires 4a, 5a and 15a. Alternatively, each of the lead wires 4a, 5a and 15a may be formed into an electrode-type capable of being plugged into a connection portion, so that the connection to the outside can be conducted simply in a snap-fitting manner. Further, an insulating cover 31 is secured to a surface of the insulating substrate 30 to cover the working electrode 4, the counter electrode 5 and the earth portion 15 from above, whereby a measuring space 32 having a function to draw a blood or the like into the measuring space by a capillary phenomenon is formed in a tip end of the working electrode 4 provided with the measuring portion 4b. The insulating substrate 30 is perforated with a small bore 33 for bringing the measuring space 32 into communication with the outside. It should be noted that the insulating substrate 30 and the cover 31 may be changed in their shape as required, and may be formed into shapes such that a liquid to be measured such as a blood can be introduced reliably and easily into the measuring space 32. Further, the surface of each of the insulating substrate 30 and the cover 31 may be formed in a state having a high affinity with a liquid to be measured, e.g., a blood, thereby facilitating the ingress of the liquid to be measured into the measuring space 32. The cover 31 may be omitted as required.

The reactive oxygen species sensor id shown in FIG. 6 is capable of measuring reactive oxygen species or the like by drawing a very small amount of a blood sampled from, for example, an earlobe into the measuring space 32 through an opening at a tip end of the measuring space 32 by a capillary phenomenon.

The operation of the present embodiment will be described below.

When any one of the reactive oxygen species sensors 1 and 1a shown in FIGS. 2 and 3 is used, the pointed tip end of the electrode is insetted into a living body, whereby the working electrode 4 and the counter electrode 5 are placed into the living body.

When the reactive oxygen species sensors 1b shown in FIG. 4 is used, the electrode section mounted at the tip end of the resinous pipe 16 is introduced into a blood vessel, a lymphatic a lymphatic vessel, a digestive organ or any of internal organs directly or utilizing a photo-fiberscope or the like, whereby the working electrode 4 and the counter electrode 5 are placed into a living body.

When the reactive oxygen species sensors 1c shown in FIG. 5 is used, the working electrode 4 and the counter electrode 5 of the electrode section mounted at the shaft portion with the pierce shaft inserted through the pierce bore 19 in the ear 18 are brought into contact with a living body portion of the pierce bore 19.

When the reactive oxygen species sensors 1d shown in FIG. 6 is used, a very small amount of a blood sampled, for example, from a earlobe is drawn into the measuring space 32 through the opening at the tip end of the measuring space 32 by the capillary phenomenon, whereby the working electrode 4 and the counter electrode 5 are brought into contact with the blood.

When the reactive oxygen species sensor 1, 1a, 1b, 1c or 1d is used in this manner in a measuring system in which a superoxide anion radical exists, the metal in the metalloporphyrin complex forming the polymerized film on the surface of the working electrode 4 is reduced by the superoxide anion radical. For example, if the metal ion is iron one, $Fe^{3+}$ is reduced to $Fe^{2+}$ by the superoxide anion radical (an equation (7)).

Then, the variable resistor VR1 is regulated to apply a voltage as large as enabling the oxidization of $Fe^{2+}$ resulting from the reduction by the superoxide anion radical, from the power source means 2 to the working electrode 4 and the counter electrode 5, thereby electrochemically re-oxidizing $Fe^{2+}$ resulting from the reduction (an equation (8)), and an electric current flowing at that time is measured.

$$Por(Fe^{3+}) + O_2^{-} . \rightarrow Por(Fe^{2+}) + O_2 \quad (7)$$

$$Por((Fe^{2+}) \rightarrow Por(Fe^{3+}) + e^{-} \quad (8)$$

In the equations (7) and (8), "Por" means porphyrin.

The electric current value detected by the working electrode 4 and the counter electrode 5 in the above manner corresponds to a concentration of the superoxide anion radical and hence, the concentration of the superoxide anion radical existing in a living body can be quantitatively detected based on the electric current value. Namely, the measurement of the concentration of the superoxide anion radical is enabled by a principle similar to the equations (5) and (6). According to the present embodiment, the electric current detected by the working electrode 4 and the counter electrode 5 can be determined quantitatively as the concentration of the superoxide anion radical by the reactive oxygen species concentration measuring means 3.

Further, in the present embodiment, the display means 10 of the reactive oxygen species concentration measuring means 3 displays the concentration of the reactive oxygen species or the like determined based on the electric current detected by the reactive oxygen species sensor 1, 1a, 1b, 1c or 1d, and the external output means 11 delivers the determined concentration toward the remotely monitoring means 12 by transmission or the like. The result of the detection of the concentration fed from the external output means 11 of the reactive oxygen species concentration measuring means 3 in the above manner is received by the receiving means 13 of the monitoring means 12, and the arithmetic operation is carried out based on the concentration of the active oxygen species or the like by an arithmetic means (not shown) to determine the health condition of a living body as a subject of measurement and the in-vitro environmental condition. Then, the concentration of the reactive oxygen species or the like and the health condition of the living body and the in vitro environmental condition can be displayed by a display means (likewise not shown). In this manner, the remote monitoring of the concentration of the reactive oxygen species or the like can be conducted.

Reactive oxygen species such as hydrogen peroxide and OH. and other radical active species such as NO and ONOO⁻ can be likewise quantitatively detected by a principle similar to that described above.

In this way, when any of the reactive oxygen species sensors 1, 1a, 1b, 1c and 1d according to the present embodiments is used, reactive oxygen species such as superoxide anion radical, hydrogen peroxide and OH. and other radical active species (NO, OONOO⁻) can be detected and quantitatively measured in not only in vivo but also in vitro environments. Therefore, the reactive oxygen species sensors can be utilized widely in various fields.

Thus, in an in vivo environment, various diseases can be specified by in vivo reactive oxygen species and other radical active species. Therefore, the specification of a disease such as cancer can be achieved by measuring a concentration of reactive oxygen species in a blood.

On the other hand, even in an in vitro environment, the perished state of a food can be observed by measuring reactive oxygen species and a concentration thereof in the food. In addition, the polluted state of water can be observed by measuring reactive oxygen species and a concentration thereof in water such as tap water and sewage.

Further, concentrations of a superoxide anion radical and a superoxide dismutase (which will be referred to as "SOD" hereinafter) which is an enzyme having a function to eliminate a superoxide anion radical can be measured by measuring the degree of elimination of the superoxide anion radical upon the addition of a sample containing SOD.

Figure 7:
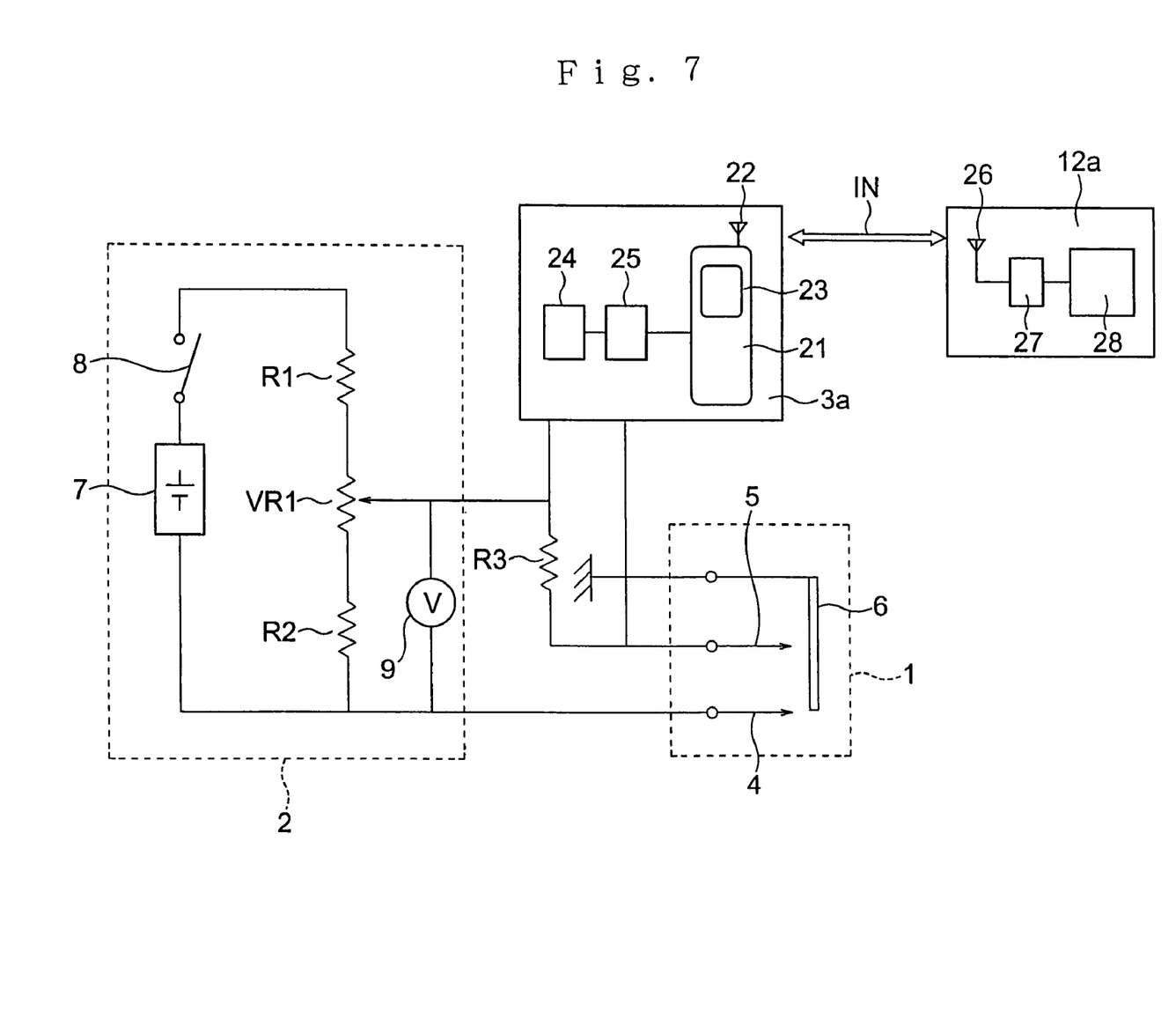
FIG. 7 is a circuit diagram showing a yet further embodiment of an active oxygen species measuring device according to the present invention.

FIG. 7 shows an alternative embodiment of the present invention further realized to enable the remote monitoring.

In this embodiment, an active oxygen species concentration measuring means 3a of a reactive oxygen species measuring device and an arrangement of a remotely monitoring means 12a are formed further particularly, and an active oxygen species sensor 1 and a power source means 2 are formed as in the embodiment shown in FIG. 1.

In this embodiment, data can be delivered and received in opposite directions between the reactive oxygen species measuring device and the remotely monitoring means 12a by utilizing an internet, and the control of the remote monitoring based on reactive oxygen species or the like can be carried out with finer contents.

Further, in the reactive oxygen species concentration measuring means 3a of the reactive oxygen species measuring device, a mobile phone 21 is provided to serve as both of a communication means 22 for transmitting and receiving data to and from the remotely monitoring means 12a and a display means 23 for displaying the data. An arithmetic control means 24 including an amplifier, CPU and a memory (all not shown) is also provided in the reactive oxygen species concentration measuring means 3a to determine a concentration of reactive oxygen species under the reception of a detected voltage fed from a reactive oxygen species sensor 1 and to convert the data into data transmittable by the mobile phone 21. Data from the arithmetic control mans 24 is transmitted through an interface 25 to the mobile phone 21. A necessary software (program) is installed in the mobile phone 21, after being supplied from the remotely monitoring means 12a serving as a base station (a host side) for carrying out the overall control of a remotely controlled active oxygen species measuring system capable of being constructed based on the present invention, so that the communication means 22 and the display means 23 are operated. The communication means 22 is configured to transmit data concerning the concentration of active oxygen species received from the arithmetic control means 24 by a mail appended with such data to the remotely monitoring means 12a through an internet IN, on the one hand, and to receive data transmitted through the internet IN from the remotely monitoring means 12a, on the other hand. The display means 23 is configured to display the data concerning the concentration of reactive oxygen species received from the arithmetic control means 24, and to display data concerning the health condition of a living body and an in-vitro environmental condition (which will be described below) received from the remotely monitoring means 12a.

In the remotely monitoring means 12 serving as the base station (the host side) for carrying out the overall control of the remotely controlled reactive oxygen species measuring system, there are a communication means 26 for transmitting and receiving data to and from the communication means 22 of the reactive oxygen species measuring device through the internet IN, an arithmetic means 27 including a CPU for carrying out a data processing for data concerning the concentration of reactive oxygen species and received from the reactive oxygen species measuring device and operating the various sections in association with one another and a memory (both not shown) and the like, and a display means 28 for displaying the concentration of reactive oxygen species or the like and the result of the data processing provided by the arithmetic means 27.

The operation of the present embodiment will be described below.

An electric current in a living body or in a portion outside a living body as a subject of measurement, which has been detected as in the embodiment shown in FIG. 1 using the reactive oxygen species sensor 1 and the power source means 2, is delivered into the reactive oxygen species concentration measuring means 3a. The arithmetic control means 24 conducts an arithmetic operation for the inputted electric current value to determine a concentration of reactive oxygen species, and further conducts a necessary data processing to transmit the result to the mobile phone 21 through the interface 25. The mobile phone 21 displays the concentration of reactive oxygen species as an image picture represented by numerical values or a graph on the display means 23 according to the instruction from the software already installed, and transmits data concerning the concentration of reactive oxygen species or the like to the remotely monitoring means 12a by a mail through the internet IN by means of the communication means 22. In the remotely monitoring means 12a, the arithmetic means 27 carries out the data processing for the data concerning the concentration of reactive oxygen species or the like and received by the communication means 27, thereby determining the health condition of a living body such as a person as a subject of measurement and an in-vitro environmental condition. Then, the concentration of reactive oxygen species as well as the health condition of the living body and the in-vitro environmental condition are displayed by the display means 28. Thus, the health condition of the living body and the like can be monitored from a remote location or place. Further, the data concerning the health condition of the living body and the like determined in the remotely monitoring means 12a are returned to the mobile phone 21e in the reactive oxygen species measuring device through the communication means 26 and 22 in the remotely monitoring means 12a and the reactive oxygen species measuring device and through the internet IN and then displayed on the display means 23. In this manner, it is possible to provide a service for informing a person in a reactive oxygen species concentration measuring filed of the data concerning the health condition of the living body and the like. In addition, a guideline for the subsequent health care can be obtained in the measuring field. By using the remotely monitoring means 12a as the base station, it is possible to make a simultaneously access to a plurality of reactive oxygen species measuring devices, to provide a centralized management for various data, and to diagnose the health condition or the diseased condition of a living body such as a person as a subject of measurement based on various data by a physician and inform a person in the concentration measuring field of the result of the diagnosis. Particular, if there is a need for the diagnosis provided based on the concentration of active oxygen species in an emergency operating field by a physician, then the diagnosis cab be conducted in real time by a physical specialist existing in a remote place, leading to a rapidness and a suitability in a lifesaving operation. Further, the data processing which is arithmetically inoperable in the reactive oxygen species measuring device can be carried out in the remotely monitoring means 12a, and necessary data provided by the arithmetic operation can be transmitted to the reactive oxygen species measuring device, which can contribute to a reduction in size of the active oxygen species measuring device. In addition, the arithmetic operation for determining the concentration of the active oxygen species based on the electric current value measured by the arithmetic control means 24 of the reactive oxygen species concentration measuring means in the reactive oxygen species measuring device may be omitted, and the measured electric current value received by the reactive oxygen species sensor 1 may be transmitted intact to the remotely monitoring means 12a, where the concentration of the reactive oxygen species or the like may be determined arithmetically from the measured electric current value. This can contribute to a further reduction in size of the reactive oxygen species measuring device. In the present embodiment, the communication means 22 and the display means 23 for the reactive oxygen species measuring device are formed by the mobile phone 21, so that the transmission and reception of the data to and from the remotely monitoring means 12a are conducted through the internet IN. Therefore, the measurement of the reactive oxygen species or the like, the remote monitoring control and the like can be carried out very easily using the mobile phone 21 excellent in portability or mobility and the internet IN.

The present invention is not limited to the above-described embodiments, and various modifications may be made as required without departing from the spirit and scope of the invention.

What is claimed is:

1. A reactive oxygen species measuring device comprising:
A reactive oxygen species sensor provided with an electrode assembly having a working electrode and a counter electrode formed into a shape enabling the detection of the presence of an in-vivo active oxygen species in terms of an electric current, said electrode assembly being selected from the group consisting of a catheter-shape capable of being inserted into a blood vessel and a pierce shaft-shape capable of being bonded to a surface of a skin,
A power source means for applying a measuring voltage to said reactive oxygen species sensor, and
A reactive oxygen species concentration measuring means for measuring a concentration of the reactive oxygen species or the like from said current detected by said reactive oxygen species sensor; and wherein
The working electrode of said reactive oxygen species sensor includes, on its surface, an element capable of detecting the presence of active oxygen species or the like in terms of an electric current;
said element capable of detecting the presence of reactive oxygen species in terms of an electric current consists of a polymerized film of a metal porphyrin complex; and
said metal porphyrin complex is represented by the following formula (II):

wherein M indicates a metal ion selected from the group consisting of iron, manganese, a cobalt, chromium and iridium; at least one of four Rs is any one of thiofuryl, pyrrolyl, furyl, mercaptophenyl, aminophenyl and hydroxyphenyl groups; and each of other Rs indicates any of the above-described groups, or alkyl group, aryl group or hydrogen; and at least one of two Ls is an nitrogen-based axial ligand such as imidazole and its derivative, pyridine and its derivative, aniline and its derivative, histidine and its derivative, and trimethylamine and its derivative, a sulfur-based axial ligand such as thiophenol and its derivative, cysteine or its derivative, and methionine and its derivative, or an oxygen-based axial ligand such as benzoic acid and its derivative, acetic acid and its derivative, phenol and its derivative, an aliphatic alcohol and its derivative or water; and the other L indicates any of the above-listed axial ligands.

2. A reactive oxygen species measuring device according to claim 1, characterized in that said reactive oxygen species concentration measuring means includes an external output means for delivering the measured concentration of the reactive oxygen species or the like to the outside, and further includes a remotely monitoring means adapted to monitor the concentration of the active oxygen species or the like under the reception of the output from said external output means.

3. An active oxygen species measuring device according to claim 2, characterized in that
said remotely monitoring means includes a communication means for transmitting and receiving data to and from said reactive oxygen species measuring device, an arithmetic means for conducting a data processing for the concentration of the reactive oxygen species or the like received from said external output means, and a display means for display the concentration of the reactive oxygen species or the like and the result of the data processing provided by said arithmetic means, and
said external output means in said reactive oxygen species measuring device is comprised of a communication means for transmitting and receiving the data to and from the remotely monitoring means, and a display means for displaying the concentration of the reactive oxygen species or the like and the data received from said remotely monitoring means.

4. A reactive oxygen species measuring device according to any of claims 1 to 3, characterized in that the electrode of said reactive oxygen species sensor is formed into a shape capable of detecting the presence of an in vivo reactive oxygen species or the like in terms of an electric current.

5. A reactive oxygen species measuring device according to any of claims 1 to 3, characterized in that said power source means is formed so that the measuring voltage to be applied to said reactive oxygen species sensor can be controlled variably.

6. A reactive oxygen species measuring device according to any of claims 1 to 3, characterized in that said reactive oxygen species concentration measuring means includes at least one of a display means for displaying a concentration of reactive oxygen species or the like determined based on the electric current detected by said reactive oxygen species sensor, and an external output means for delivering data to the outside.

7. A remotely controlled reactive oxygen species measuring system according to claim 2 or 3, characterized in that the delivery and reception of the data between said reactive oxygen species measuring device and said remotely monitoring means are carried out through a radio or wire propagation system.

8. A remotely controlled reactive oxygen species measuring system according to claim 2 or 3, characterized in that the communication means and the display means of said reactive oxygen species measuring device are formed in a mobile phone to deliver and receive the data to and from said remotely monitoring means through an internet.

9. A reactive oxygen species measuring device according to claim 1, characterized in that the porphyrin compound forming said metal porphyrin complex is one selected from the group consisting of 5,10,15,20-tetrakis(2-thienyl)porphyrin, 5,10,15,20-tetrakis(3-thienyl)porphyrin, 5,10,15,20-tetrakis(2-pyrrolyl)porphyrin, 5,10,15,20-tetrakis(3-pyrrolyl)porphyrin, 5,10,15,20-tetrakis(2-furyl)porphyrin, 5,10,15,20-tetrakis(3-furyl)porphyrin, 5,10,15,20-tetrakis(2-mercaptophenyl)porphyrin, 5,10,15,20-tetrakis(3-mercaptophenyl)porphyrin, 5,10,15,20-tetrakis(4-mercaptophenyl)porphyrin, 5,10,15,20-tetrakis(2-aminophenyl)porphyrin, 5,10,15,20-tetrakis(3-aminophenyl)porphyrin, 5,10,15,20-tetrakis(4-aminophenyl)porphyrin, 5,10,15,20-tetrakis(2-hydroxyphenyl)porphyrin, 5,10,15,20-tetrakis(3-hydroxyphenyl)porphyrin, 5,10,15,20-tetrakis(4-hydroxyphenyl)porphyrin, [5,10,15-tris(2-thienyl)-20-mono(phenyl)]porphyrin, [5,10,15-tris(3-thienyl)-20-mono(phenyl)]porphyrin, [5,10-bis(2-thienyl)-15,20-di(phenyl)]porphyrin, [5,10-bis(3-thienyl)-15,20-di(phenyl)]porphyrin, [5,10-bis(2-thienyl)-10,20-di(phenyl)]porphyrin, [5,10-bis(3-thienyl)-10,20-di(phenyl)]porphyrin, [5-mono(2-thienyl)-10,15,20-tri(phenyl)]porphyrin, [5-mono(3-thienyl)-10,15,20-tri(phenyl)]porphyrin.

10. The reactive oxygen species measuring device according to claim 1, wherein R=4.

* * * * *